United States Patent
Kanakasabai et al.

(10) Patent No.: US 10,317,484 B2
(45) Date of Patent: Jun. 11, 2019

(54) METHOD AND SYSTEM FOR CONTACTLESS POWER TRANSFER IN A GATE DRIVER UNIT

(71) Applicant: General Electric Company, Schenectady, NY (US)

(72) Inventors: Viswanathan Kanakasabai, Bangalore (IN); Adnan Kutubuddin Bohori, Bangalore (IN); Rajendra Naik, Bangalore (IN); Suma Memana Narayana Bhat, Bangalore (IN); Arun Kumar Raghunathan, Bangalore (IN)

(73) Assignee: General Electric Company, Schenectady, NY (US)

( * ) Notice: Subject to any disclaimer, the term of this patent is extended or adjusted under 35 U.S.C. 154(b) by 23 days.

(21) Appl. No.: 15/517,132

(22) PCT Filed: Oct. 8, 2015

(86) PCT No.: PCT/US2015/054719
§ 371 (c)(1),
(2) Date: Apr. 5, 2017

(87) PCT Pub. No.: WO2016/057804
PCT Pub. Date: Apr. 14, 2016

(65) Prior Publication Data
US 2017/0307702 A1    Oct. 26, 2017

(30) Foreign Application Priority Data
Oct. 9, 2014   (IN) ........................... 5089/CHE/2014

(51) Int. Cl.
*G01V 3/00*   (2006.01)
*G01R 33/385*   (2006.01)
(Continued)

(52) U.S. Cl.
CPC .......... *G01R 33/3852* (2013.01); *A61B 5/055* (2013.01); *G01R 33/36* (2013.01)

(58) Field of Classification Search
CPC .. H02J 5/005; H02J 7/025; H02J 50/12; H02J 50/50; H02J 50/80; H02J 50/90;
(Continued)

(56) References Cited

U.S. PATENT DOCUMENTS 9,352,661 B2 *   5/2016   Keeling .............. B60L 11/1829
9,929,595 B2 *   3/2018   Mao ........................ H02J 7/025
(Continued)

FOREIGN PATENT DOCUMENTS

KR   10-2014-0095348 A   8/2014
WO   2013156889 A1   10/2013

OTHER PUBLICATIONS

International Search Report and Written Opinion for International Application No. PCT/US2015/054719, dated Jan. 26, 2016, 2 pages.

*Primary Examiner* — Thang X Le

(57) ABSTRACT

A gate driver unit is presented. The gate driver unit includes a first power exchanging coil operatively coupled to a power source. The gate driver unit includes a second power exchanging coil configured to receive power from the first power exchanging coil via a magnetic field and a field focusing element disposed between the first power exchanging coil and the second power exchanging coil and configured to focus the magnetic field onto the second power exchanging coil. The gate driver unit also includes a first circuit coupled to the second power exchanging coil. The gate driver unit includes a gate drive subunit operatively coupled to the first circuit and configured to provide an output signal to a control terminal corresponding to a controllable switch of a second circuit. A magnetic resonance imaging system and a method of contactless power
(Continued)

transfer in a magnetic resonance imaging system are also presented.

28 Claims, 6 Drawing Sheets

(51) Int. Cl.
*A61B 5/055* (2006.01)
*G01R 33/36* (2006.01)

(58) Field of Classification Search
CPC . H02M 3/158; H02M 3/33592; B60L 11/182; B60L 11/1825; B60L 11/1833; Y02T 90/14; Y02T 90/121; Y02T 90/122; Y02T 90/125; Y02T 90/128
See application file for complete search history.

(56) References Cited

U.S. PATENT DOCUMENTS

| | | | |
|---|---|---|---|
| 2005/0226380 A1 | 10/2005 | Katch et al. | |
| 2011/0163542 A1* | 7/2011 | Farkas | B60L 11/005 290/2 |
| 2012/0245649 A1* | 9/2012 | Bohori | A61N 1/3787 607/9 |
| 2014/0062181 A1 | 3/2014 | Bohori et al. | |
| 2014/0139041 A1 | 5/2014 | Bohori et al. | |
| 2015/0194811 A1* | 7/2015 | Mao | H02J 7/025 307/104 |
| 2015/0229132 A1* | 8/2015 | Katsunaga | H02J 50/80 307/104 |
| 2016/0294227 A1* | 10/2016 | Podkamien | H02J 5/00 |

\* cited by examiner

METHOD AND SYSTEM FOR CONTACTLESS POWER TRANSFER IN A GATE DRIVER UNIT

CROSS-REFERENCE TO RELATED APPLICATIONS

This is a national stage application under 35 U.S.C. § 371 (c) of PCT Patent Application No. PCT/US2015/054719, filed on Oct. 8, 2015, which claims priority to India Patent Application No. 5089/CHE/2014, filed on Oct. 9, 2014, the disclosures of which are incorporated herein by reference in their entireties.

BACKGROUND

Embodiments of the present disclosure generally relate to a gate driver and specifically to a system and method for contactless power transfer in a gate driver of a high voltage system, a medium voltage system, or a low voltage system. More particularly, the present disclosure relates to a Magnetic Resonance Imaging (MRI) system.

In general, MRI systems include several subsystems such as a gradient amplifier, a radio frequency (RF) amplifier, an RF receiver, a patient handling system, an oxygen monitor, and a cryo-cooler. Furthermore, equipment from the MRI system is typically spread across multiple rooms in a hospital, such as an equipment room, a scan room, and a radiologist/control room. Conventionally, most of the MRI subsystems are placed in an equipment room. In recent times, there have been attempts to move many of these MRI subsystems to the scan room from the equipment room, in order to reduce the footprint of the equipment room.

Generally, these subsystems include electrical circuitry which involves use of ferrite/magnetic components. In one example, the electrical circuitry includes a power transfer system for the gate drivers employed within the gradient amplifier. The power transfer system for the gate drivers has several transformers with a ferrite core. These transformers in the power transfer system for the gate driver aid in providing necessary isolation and a high dv/dt immunity. However, since the scan room employs high powered magnets, with magnetic fields typically in the 1.5 Tesla to 3 Tesla range, the subsystems to be placed in the scan room should be devoid of ferrite/magnetic components in order to avoid risk of magnetic saturation.

Moreover, the movement of the gradient amplifier to the scan room restricts frequency of operation of the semiconductor devices in different subsystems, including the power transfer system for the gradient amplifier gate driver since the frequency of operation of the gradient amplifier gate driver can interfere with Larmor or precessional frequency of the MRI system, thereby compromising the imaging quality of the MRI system.

SUMMARY

In accordance with aspects of the present disclosure, a gate driver unit is presented. The gate driver unit includes a first power exchanging coil operatively coupled to a power source. Further, the gate driver unit includes a second power exchanging coil configured to receive power from the first power exchanging coil via a magnetic field. In addition, the gate driver unit includes a field focusing element disposed between the first power exchanging coil and the second power exchanging coil and configured to focus the magnetic field onto the second power exchanging coil. The gate driver unit also includes a first circuit coupled to the second power exchanging coil. Moreover, the gate driver unit includes a gate drive subunit operatively coupled to the first circuit and configured to provide an output signal to a control terminal corresponding to a controllable switch of a second circuit.

In accordance with another aspect of the present disclosure, a magnetic resonance imaging system is presented. The magnetic resonance imaging system includes a gradient amplifier disposed proximate to a magnet assembly of the magnetic resonance imaging system and comprising a plurality of controllable switches. Furthermore, the magnetic resonance imaging system includes a gate driver unit operatively coupled to the gradient amplifier. The gate driver unit includes a first power exchanging coil operatively coupled to a power source. Moreover, the gate driver unit includes a second power exchanging coil configured to receive power from the first power exchanging coil via a magnetic field. The gate driver unit also includes a field focusing element disposed between the first power exchanging coil and the second power exchanging coil and configured to focus the magnetic field onto the second power exchanging coil and to enhance coupling between the first power exchanging coil and the second power exchanging coil. Further, the gate driver unit includes a first circuit coupled to the second power exchanging coil. In addition, the gate driver unit includes a gate drive subunit operatively coupled to the first circuit and configured to provide an output signal to a control terminal corresponding to the plurality of controllable switches.

In accordance with yet another aspect of the present disclosure, a method of contactless power transfer in a magnetic resonance imaging system, is presented. The method includes transferring power from a power source via at least one of a first power exchanging coil, a field focusing element, and a second power exchanging coil to a gate drive subunit. Furthermore, the method includes switching a controllable switch of a gradient amplifier based on an output signal provided to a control terminal of the controllable switch from the gate drive subunit. In addition, the method includes transferring data between the gradient amplifier to a control subunit via at least one of the gate drive subunit, the second power exchanging coil, the field focusing element, and the first power exchanging coil.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this specification belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean one, some, or all of the listed items. The use of "including," "comprising" or "having" and variations thereof herein are meant to encompass the items listed thereafter and equivalents thereof as well as additional items. The terms "connected" and "coupled" are not restricted to physical or mechanical connections or couplings, and can include electrical connections or couplings, whether direct or indirect. Furthermore, terms "circuit" and "circuitry" and "controller" may include either a single component or a plurality of components, which are either active and/or passive and are connected or otherwise coupled together to provide the described function. Also, the term operatively coupled as used herein includes wired coupling, wireless coupling, electrical coupling, magnetic coupling, radio communication, software based communication, or combinations thereof.

As will be described in detail hereinafter, an exemplary embodiment of a gate driver unit is presented. Specifically, an exemplary embodiment of the gate driver unit as used in a magnetic resonance imaging (MRI) system and a method of contactless power transfer in the gate driver unit as used in the MRI system are also presented. In accordance with aspects of the present disclosure, the gate driver unit is devoid of ferrites facilitating the positioning of the gate driver unit proximate to a magnetic assembly of the MRI system. Accordingly, a gradient amplifier of an MRI system which employs the gate driver unit may be positioned in a scan room, proximate to the magnetic assembly of the MRI system. This in turn aids in reducing the footprint of an equipment room for the MRI system.

Figure 1:
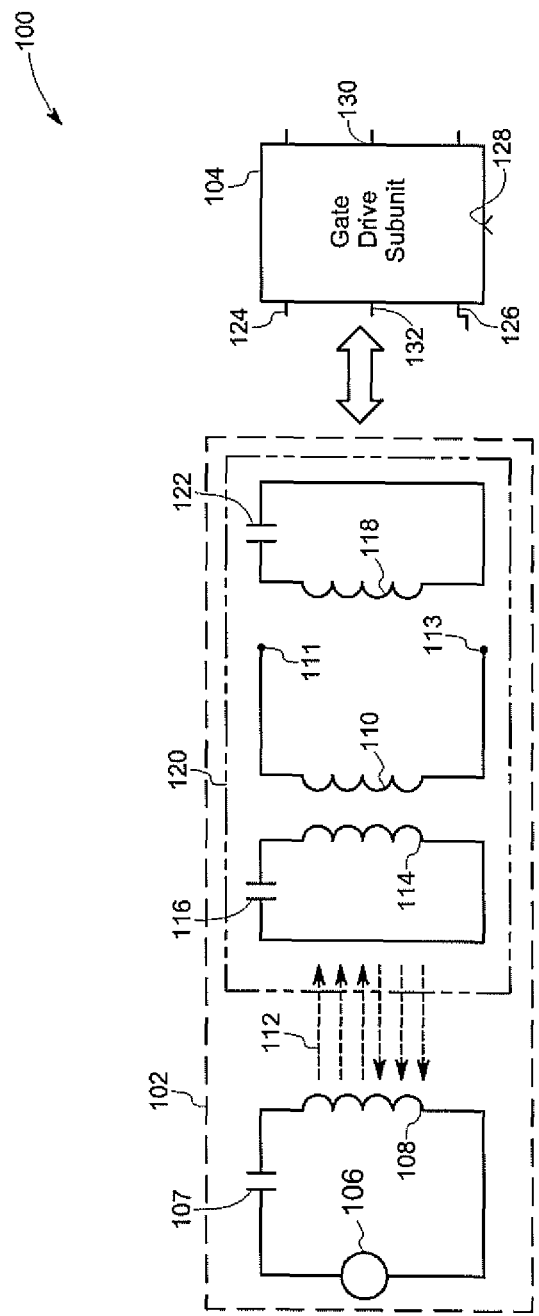
FIG. 1 is a diagrammatical representation of an exemplary gate driver unit, according to embodiments of the present invention.

Referring to FIG. 1, a diagrammatical representation of an exemplary gate driver unit 100, according to embodiments of the present invention, is depicted. The gate driver unit 100 includes a contactless power transfer subunit 102 and a gate drive subunit 104. In one example, the gate driver unit 100 is disposed on a printed circuit board. In particular, the gate driver unit 100 may be fabricated on a printed circuit board. The contactless power transfer subunit 102 includes a first power exchanging coil 108, a second power exchanging coil 110, a field focusing element 114, and a compensation coil 118. In one embodiment, the gate drive subunit 104 generates a signal for controlling switching of a controllable switch. In one example, the gate drive subunit 104 is made of a combination of logic gates.

Moreover, the gate driver unit 100 includes a power source 106. The power source 106 is operatively coupled to the first power exchanging coil 108 via a coil capacitor 107.

In one example, the power source 106 may provide an alternating current (AC) quantity. The contactless power transfer subunit 102 aids in transferring power from the power source 106 to the gate drive subunit 104. In the example of FIG. 1, the power is provided via the contactless power transfer subunit 102 to terminals 124 and 126 of the gate drive subunit 104. In particular, terminal 111 of the second power exchanging coil 110 is coupled to the terminal 124 and terminal 113 of the second power exchanging coil 110 is coupled to the terminal 126 via any associated electronics. The associated electronics includes a rectifier and capacitors, in one example. The rectifier may include an active rectifier or a diode rectifier. In one non-limiting example, +15 volts is provided at the terminal 124 and −5 volts is provided at the terminal 126, with respect to an isolated ground terminal 132. The example of FIG. 1 represents a single gate drive subunit 104. However, use of multiple gate drive subunits is anticipated. The gate drive unit 100 is explained in greater detail with respect to FIG. 3.

Furthermore, the first power exchanging coil 108 is operatively coupled to the second power exchanging coil 110. In particular, the first power exchanging coil 108 is wirelessly coupled to the second power exchanging coil 110. In one example, the first power exchanging coil 108 is magnetically coupled to the second power exchanging coil 110. In one non-limiting example, the first power exchanging coil 108 and the second power exchanging coil 110 are separated by an insulator, an air gap, or a combination thereof.

In addition, the field focusing element 114 may be disposed between the first power exchanging coil 108 and the second power exchanging coil 110. The field focusing element 114 includes a resonator. In one example, the resonator is a resonating coil. Moreover, in the example of FIG. 1, end terminals of the field focusing element 114 are coupled to a field focusing capacitor 116. The coupling of the first power exchanging coil 108 and the second power exchanging coil 110 via the field focusing element 114 may be referred to as resonance coupling. The term resonance coupling, as used herein, may be used to refer to coupling between two power exchanging coils such that the power exchanging coils are able to exchange power when excited at a desired resonant frequency. According to aspects of the present disclosure, the field focusing element 114 operates at at least one resonant frequency. The power, as well as data and control signals, are transferred at the at least one resonant frequency of the field focusing element 114. In one example, the power, data and control signals are transferred simultaneously at three different resonant frequencies of the field focusing element 114. Furthermore, in another example, the power, data, and control signals, or combinations thereof are transferred alternately at the at least one resonant frequency of the field focusing element 114. The first power exchanging coil 108 and the second power exchanging coil 110 are configured to handle a bidirectional flow of the power, data, and control signals between the first power exchanging coil 108 and the second power exchanging coil 110. The term bidirectional flow as used herein may be used to refer to to-and-from transmission.

For example, in one embodiment, the first power exchanging coil 108 may be configured to operate as a transmitter coil and the second power exchanging coil 110 may be configured to operate as a receiver coil. However, in another embodiment, the first power exchanging coil 108 may be configured to operate as a receiver coil and the second power exchanging coil 110 may be configured to operate as a transmitter coil based on operational requirements.

In an embodiment where the first power exchanging coil 108 behaves as the transmitter coil and the second power exchanging coil 110 behaves as the receiver coil, the first power exchanging coil 108 receives power from the power source 106 and converts the received power into a magnetic field 112. The first power exchanging coil 108 transmits the magnetic field 112 to the field focusing element 114. Furthermore, the field focusing element 114 focuses the magnetic field onto the second power exchanging coil 110. In particular, the field focusing element 114, upon excitation, amplifies the magnetic field 112 received from the first power exchanging coil 108 and transmits an amplified magnetic field to the second power exchanging coil 110. Accordingly, the power is transmitted to the second power exchanging coil 110 via the magnetic field. Different embodiments of the field focusing element 114 will be explained in greater detail with respect to FIGS. 4 and 5.

In the example of FIG. 1, the compensation coil 118 is operatively coupled to the second power exchanging coil 110. In particularly, the compensation coil 118 and the second power exchanging coil 110 are wirelessly coupled. Furthermore, the compensation coil 118 is operatively coupled to a compensation coil capacitor 122. The second power exchanging coil 110, the field focusing element 114, and the compensation coil 118 are wirelessly coupled to each other in a relatively fixed position and together form a power transfer element 120. The compensation coil 118 matches impedance of the first power exchanging coil 108 and the power transfer element 120. In one example, the compensation coil 118 is configured to match impedance of the first power exchanging coil 108 to the second power exchanging coil 110.

Also, the compensation coil 118 aids in compensating for any change is phase angle resulting from any misalignment between the first power exchanging coil 108 and the power transfer element 120. In one non-limiting example, the compensation coil 118 aids in compensating for any change is phase angle resulting from any misalignment between the first power exchanging coil 108 and the second power exchanging coil 110. As used herein, the term misalignment may be used to refer to any angular deviation between a first power exchanging coil, such as the first power exchanging coil 108, and a power transfer element, such as the power transfer element 120. Since the second power exchanging coil 110, the field focusing element 114, and the compensation coil 118 are coupled to each other in a relatively fixed position, any misalignment will likely be between the first power exchanging coil 108 and the power transfer element 120. Also, this misalignment should not be interpreted as a misalignment between individual components of the power transfer element 120. Additionally, the compensation coil 118 aids in enhancing coupling between the first power exchanging coil 108 and the power transfer element 120.

In one embodiment, the compensation coil 118 and the field focusing element 114, each operate at different resonant frequencies with respect to each other. In one embodiment, the resonant frequency of the compensation coil 118 is higher than the resonant frequency of the field focusing element 114. In one non-limiting example, the compensation coil 118 operates at twice the resonant frequency of the field focusing element 114. Accordingly, the compensation coil 118 behaves as a capacitor due to the relatively higher resonant frequency as compared to the resonant frequency of the field focusing element 114 and therefore, the power transfer element 120 may have a capacitive reactance. This aids in compensating for a lagging power factor in the contactless power transfer subunit 102.

This capacitive reactance increases input power factor of the contactless power transfer subunit 102. An efficiency of the contactless power transfer subunit 102 depends on the input power factor of the contactless power transfer subunit 102. Therefore, with the increased input power factor, the efficiency of the contactless power transfer subunit 102 is considerably enhanced. Due to the enhanced efficiency, power transfer capability of the contactless power transfer subunit 102 improves considerably. Accordingly, the first power exchanging coil 108 and the power transfer element 120 may have enhanced coupling between each other.

In another embodiment, the resonant frequency of the compensation coil 118 is lower than the resonant frequency of the field focusing element 114. This provides an inductive reactance to the power transfer element 120 and compensates for a leading power factor in the contactless power transfer subunit 102.

As noted hereinabove, data and control signals may be transferred between the first power exchanging coil 108 and the second power exchanging coil 110. The data may include temporally separated first data and second data. The first data, for example, may include a polling signal provided to a circuit such as, but not limited to an amplifier, a rectifier, an inverter, and a converter, from a control subunit (not shown) via the contactless power transfer subunit 102. The circuit may be an electronic sub-assembly, in one non-limiting example. In a MRI system the first data may include a polling signal provided to a circuit such as a gradient amplifier, gradient coils, gradient control unit, and the like. The second data may include health monitoring data corresponding to the circuit. This second data may be transferred from the circuit to the control subunit via the second power exchanging coil 110, the field focusing element 114, and the first power exchanging coil 108. Moreover, in one specific example the first data may include a request to a circuit to transmit second data in the form of health monitoring data corresponding to the circuit.

Also, the control signals transferred between the first power exchanging coil 108 and the second power exchanging coil 110 may include a first control signal and a second control signal. The first control signal may include an input signal to be provided to the gate drive subunit 104. In particular, the first control signal may be provided at a terminal 128 of the gate drive subunit 104. In one example, the first control signal ranging from zero to 5 volts may be provided from the control subunit to the gate drive subunit 104 via the first power exchanging coil 108, the second power exchanging coil 110, and the field focusing element 114. In another example, the first control signal may be provided from the control subunit to the gate drive subunit 104 via an isolated fiber optic cable, an opto-coupler, or a combination thereof. The second control signal may include a feedback signal. The transfer of the data and the control signals and the function of the data and the control signals will be explained in greater detail with respect to FIG. 3.

Furthermore, an output signal of the gate drive subunit 104 may be obtained at terminal 130. In one embodiment, the output signal of the gate drive subunit 104 may be determined based on the first control signal provided at the terminal 128 of the gate drive subunit 104. In another embodiment, the output signal of the gate drive subunit 104 may be determined based on the first control signal provided at the terminal 128 of the gate drive subunit 104 as well as the health monitoring data corresponding to the circuit. Furthermore, the output signal of the gate drive subunit 104 may be provided to a control terminal of one or more controllable switches of a circuit such as a gradient amplifier. The output signal may determine if the controllable switch of the circuit is to be activated or deactivated. In a non-limiting example, the controllable switch may include an insulated gate bipolar transistor, a metal oxide semiconductor field effect transistor, a field effect transistor, a gate turn-off thyristor, an insulated gate commutated thyristor, an injection enhanced gate transistor, a silicon carbide based switch, a gallium nitride based switch, a gallium arsenide based switch, a micro-electromechanical systems based switch, or combinations thereof. In addition, the control terminal of the controllable switch may include a gate terminal.

According to aspects of the present disclosure, the gate driver unit 100 is devoid of ferrites. Also, due to separation between the first power exchanging coil 108 and the second power exchanging coil 110 a high dv/dt immunity is achieved. Accordingly, a leakage current of the gate driver unit 100 is reduced. According to aspects of the present disclosure, the gate driver unit 100 aids in transmitting power efficiently from the power source 106 to an external circuit component such as a controllable switch. The gate driver unit 100 as used in a MRI system will be explained in greater detail with respect to FIGS. 2-3. Also, the method of contactless power transfer in gate driver unit 100 as used in a MRI system will be explained in greater detail with respect to FIG. 6.

Figure 2:
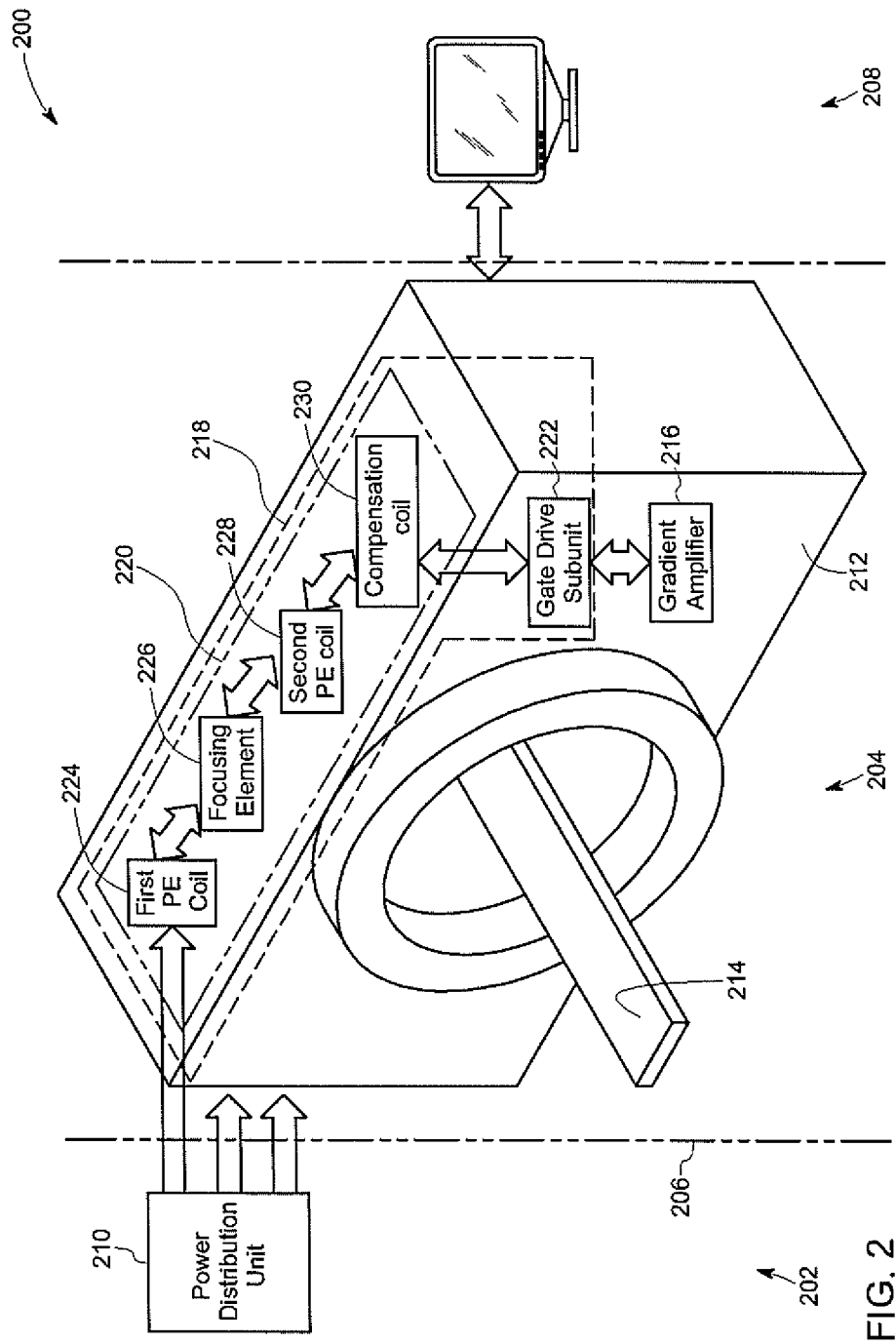
FIG. 2 is a diagrammatical representation of an exemplary embodiment of the gate driver unit as used in a magnetic resonance imaging system, according to embodiments of the present invention.

Turning now to FIG. 2, a diagrammatical representation of an exemplary embodiment of a gate driver unit, such as the gate driver unit 100 of FIG.1, as used in a magnetic resonance imaging system 200, is presented. The MRI system 200 may include a plurality of components which may be distributed across a first location 202, a second location 204, and a third location 208. By way of example, the first location 202 may be an equipment room, the second location 204 may be a scan room, and the third location 208 may be a radiologist room. The radiologist room may include an user interface device to display images obtained from a MRI scan for a radiologist or a system operator to view. The location 204 is magnetically shielded to avoid any external magnetic fields from distorting the MRI scan images. Moreover, the first location 202 and the second location 204 may be separated by a penetration wall 206. The power and control cables run between the two locations 204, 206 via the penetration wall 206.

The MRI system 200 may include a power distribution unit (PDU) 210, a MRI scanner 212, and a patient table 214. The PDU 210 may be positioned at the first location 202, and the MRI scanner 212 and the patient table 214 may be positioned at the second location 204.

The MRI scanner 212 includes a magnet assembly, where the magnet assembly includes a plurality of coils. In one example, the coils may include RF coils and gradient coils. Although not specifically shown, the MRI scanner 212 may further include an RF transmit and receive chain and additional amplification circuitry for driving the RF coils. The gradient coils may include an X-axis coil, a Y-axis coil, and a Z-axis coil. The MRI scanner 212 may further include a gradient amplifier 216 which includes an X-axis amplifier, a Y-axis amplifier, and a Z-axis amplifier, which in turn are coupled to the X-axis coil, the Y-axis coil, and the Z-axis coil, respectively. In addition, these amplifiers may include a plurality of controllable switches. The controllable switches of the amplifiers may be switched in a certain pattern to appropriately amplify an input signal provided to the amplifiers and to transfer a desired current wave shape to the X-axis or Y-axis or Z-axis coil. The MRI system 200 may further include a plurality of auxiliary units such as a cryo cooler, a body resonant magnet (BRM) chiller, and the like.

In accordance with aspects of the present disclosure, rather than being located remotely in location 202 in isolation from the MRI scanner the gradient amplifier 216 is proximate to the MRI scanner 212 at the second location 204. In particular, the gradient amplifier 216 may be disposed proximate to a magnetic assembly including high powered magnets, with a magnetic field typically in the 1.5 Tesla to 3 Tesla range. This helps avoid excessive cables needing to be run between the two locations 202 and 204 and may also reduce the footprint of the location 202. However, since in accordance with aspects of the present disclosure, the gradient amplifier 216 is positioned in the location 204 having high powered magnets, all components employed in conjunction with the gradient amplifier 216 must be devoid of ferrites in order to avoid saturation in the location 204. Also, the operating frequency of the components employed with the gradient amplifier 216 must not interfere with the Larmor frequency.

In accordance with aspects of the present disclosure, the MRI system 200 at location 204 further includes a novel gate driver unit 218 including a contactless power transfer sub-unit 220 that is devoid of ferrites and is capable of operating proximate to the magnetic assembly at non-Larmor frequencies. The gate drive unit 218 may be configured to control switching of the controllable switches of the X-axis amplifier, the Y-axis amplifier, and the Z-axis amplifier corresponding to the gradient amplifier. In one example, the gate driver unit 218 is operatively coupled with the gradient amplifier 216. In another example, the gate driver unit 218 may be an integral part of the gradient amplifier 216.

In accordance with aspects of the present disclosure, the gate driver unit 218 includes a contactless power transfer subunit 220 similar in form to contactless power transfer subunit 102 of FIG. 1 and a gate drive subunit 222 similar in form to gate drive subunit 104 of FIG. 1. The contactless power transfer subunit 220 may include the first power exchanging coil 224 and a second power exchanging coil 228. A field focusing element 226 is disposed between the first power exchanging coil 224 and the second power exchanging coil 228. Furthermore, the gate driver unit 218 includes a compensation coil 230. In accordance with aspects of the present disclosure, the first power exchanging coil 224 and the second power exchanging coil 228 are separated by an insulator, an air gap, or a combination thereof. Accordingly, no ferrites are placed between the first power exchanging coil 224 and the second power exchanging coil 228. Moreover, the field focusing element 226 and the compensation coil 230 may be designed such that the resonant frequency corresponding to the field focusing element 226 and the compensation coil 230 do not interfere with the Larmor frequency of the MRI system 200.

The PDU 210 may include a high frequency power transformer or a line frequency transformer and associated electronics. In addition, the PDU 210 may generate one or more DC voltages as an output. This output is provided to the different components of the MRI system 200 such as, but not limited to the gradient amplifier, the RF transmit chain, and the RF receive chain. Furthermore, the first power exchanging coil 224 of the contactless power transfer subunit 220 receives power from the PDU 210. In particular, at least one DC voltage is provided as an input to a first power exchanging coil 224 from the PDU 210. More particularly, the DC voltage is converted into a high frequency AC and then provided as an input to the first power exchanging coil 224. The first power exchanging coil 224 converts the voltage from the PDU into a magnetic field, such as the magnetic field 112 of FIG. 1. The field focusing element 226 focuses the magnetic field transmitted by the first power exchanging coil 224 onto the second power exchanging coil 228. Accordingly, the power is transmitted to the second power exchanging coil 228 via the magnetic field. The field focusing element 226 includes a resonator. Functioning of the first power exchanging coil, the field focusing element, the second power exchanging coil, and the compensation coil are similar to that described with respect to FIG. 1.

Figure 3:
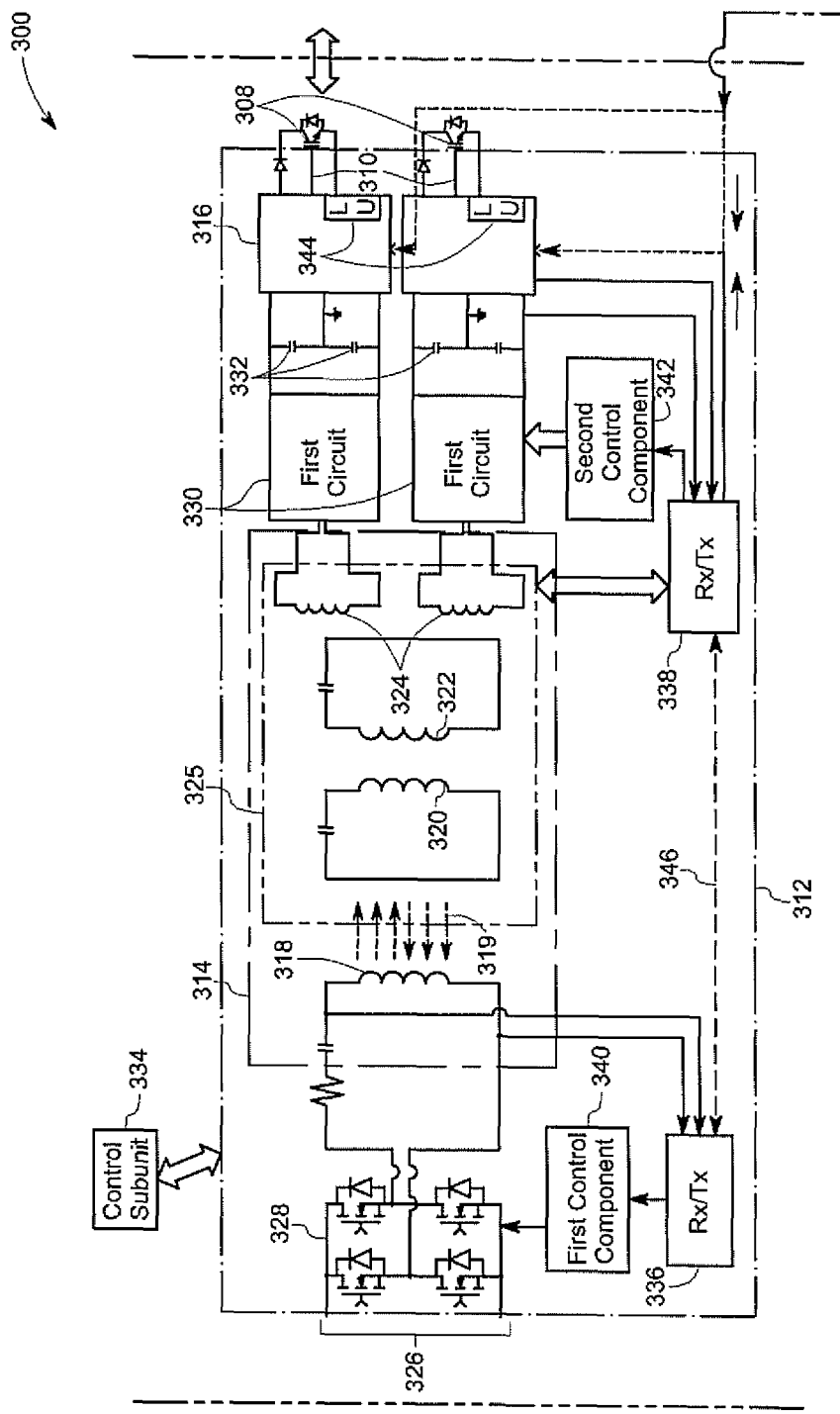
FIG. 3 is another diagrammatical representation of an exemplary embodiment of the gate driver unit as used in the magnetic resonance imaging system, according to embodiments of the present invention.

FIG. 3 is a more detailed representation of a gate driver unit within a magnetic resonance imaging system 300, according to embodiments of the present invention. As with MRI system 200, the MRI system 300 may include a plurality of components distributed across multiple locations. More specifically, MRI system 300 may include a power distribution unit (PDU), a MRI scanner, a patient table and one or more subsystems such as a gradient amplifier, a gradient control unit, a radio frequency (RF) transmit chain, a RF receive chain, a control element, and a patient handling unit.

The MRI scanner includes a magnet assembly and a plurality of coils including gradient coils and RF coils. The RF transmit and receive chain may include an additional amplification circuitry for driving the RF coils, while the gradient coils may include an X-axis coil, a Y-axis coil, and a Z-axis coil. In one example, the gradient amplifier, may include an X-axis amplifier, a Y-axis amplifier, and a Z-axis amplifier which are in turn coupled to the X-axis coil, the Y-axis coil, and the Z-axis coil, respectively. In the illustrated embodiment of FIG. 3, the X-axis amplifier, the Y-axis amplifier, and the Z-axis amplifier include a plurality of controllable switches 308. The plurality of controllable switches 308 may include an insulated gate bipolar transistor, a metal oxide semiconductor field effect transistor, a field effect transistor, a gate turn-off thyristor, an insulated gate commutated thyristor, an injection enhanced gate transistor, a silicon carbide based switch, a gallium nitride based switch, a gallium arsenide based switch, a micro-electromechanical systems based switch, or combinations thereof. Moreover, the controllable switch 308 may include a control terminal such as control terminal 310. The control terminal 310 of the controllable switch 308 may further include a gate terminal.

MRI system 300 further includes a gate driver unit 312 for controlling the switching of the plurality of controllable switches 308. The gate driver unit 312 is similar to the gate driver unit 218 of FIG. 2 and includes a contactless power transfer subunit 314 and a gate drive subunit 316. Moreover, the gate drive unit 312 may include associated electronics, such as, but not limited to an active rectifier 328, a first circuit 330, capacitors 332, control components 340, 342, and transmit receive elements 336, 338. The contactless power transfer subunit 314 includes a first power exchanging coil 318, a field focusing element 320, a compensation coil 322, and a second power exchanging coil 324. The gate driver unit 312 receives from a PDU at least one DC voltage, which may be provided across a terminal 326 of the active rectifier 328. In one example, power is provided across the terminal 326 and this power may be provided to an active rectifier 328.

The active rectifier 328 may be an H-bridge circuit, for example. Subsequently, the power is provided to the first power exchanging coil 318. The first power exchanging coil 318 converts the power into a magnetic field 319. The field focusing element 320 focuses the magnetic field 319 transmitted by the first power exchanging coil 318 onto the second power exchanging coil 324. Accordingly, the power is transmitted to the second power exchanging coil 324 via the magnetic field. In the illustrated embodiment of FIG. 3, the second power exchanging coil 324 is represented by two separate coils. The power from the second power exchanging coil 324 is provided to the first circuit 330. In the example of FIG. 3, the first circuit 330 is represented by two separate circuit blocks. In the illustrated embodiment, the first circuit 330 is a diode rectifier. In another example, the first circuit 330 may be an active rectifier that has active switches. In yet another example, the first circuit 330 may be an H-bridge circuit. Furthermore, the first circuit 330 may be operatively coupled to the gate drive subunit 316 via capacitors 332.

In the embodiment of FIG. 3, the compensation coil 322 is disposed between first power exchanging coil 318 and the second power exchanging coils 324. The compensation coil 322 matches an impedance of the first power exchanging coil 318 and the second power exchanging coils 324. Moreover, the compensation coil 322 compensates any change in phase angle resulting from a misalignment of the first power exchanging coil 318 and the second power exchanging coils 324. In an embodiment such as that depicted in FIG. 3 where two second power exchanging coils 324 are provided power from a single first power exchanging coil 318, there may be a change in phase angle resulting from a misalignment between the first power exchanging coil 318 and the two second power exchanging coils 324. This misalignment may be compensated by the use of compensation coil 322. The second power exchanging coils 324, the field focusing element 320, and the compensation coil 322 may be coupled to each other in a relatively fixed position to form a power transfer element 325. The power transfer element 325 is similar in form to the power transfer element 120 of FIG. 1.

The field focusing element 320 may be configured to operate at at least one resonant frequency. The first power exchanging coil 318 and the second power exchanging coil 324 are configured to handle a bidirectional flow of the power, as well as data and control signals between the first power exchanging coil 318 and the second power exchanging coil 324 at the resonant frequency or frequencies of the field focusing element 320. In one embodiment, the data and the control signals may be transferred between the second power exchanging coils 324 to the first power exchanging coil 318 at the one or more resonant frequencies of the field focusing element 320. The one or more resonant frequencies of the field focusing element 320 may be designed such that these resonant frequencies do not interfere with Larmor frequency of the MRI system 300.

In one example, the data and the control signals may be transferred at the same resonant frequency as the resonant frequency for the transfer of power from the first power exchanging coil 318 to the second power exchanging coils 324. In particular, the power, the data, and the control signals may be alternately transferred in a sequential fashion at the same resonant frequency by way of a control switch, for example. In this scenario, when power is being transferred other quantities such as the data and control signals may not be transferred.

In another embodiment, data, power, and control signals may be transferred between the first power exchanging coil 318 and the second power exchanging coils 324 simultaneously at three different resonant frequencies. In yet another embodiment, when the data is not being transferred between the first power exchanging coil 318 and the second power exchanging coils 324, the control signal may be transferred simultaneously with the transfer of power by using two different resonant frequencies. The power, data and control signals may take a variety of forms and perform different functions. The data may be as simple as an AC or DC signal or as complex as information packetized according to one or more communications protocols.

In one embodiment, the data are transferred between the first power exchanging coil 318 and the second power exchanging coils 324. The data may include first data in the form of a polling signal which is transmitted to the gradient amplifier and second data representing health monitoring data which is transmitted from the gradient amplifier based on the first data. The health monitoring data corresponds to the health of the gradient amplifier. The health monitoring data may include a temperature, a voltage, or a current level corresponding to the gradient amplifier. In one alternate example, the health monitoring data may include a fault signal corresponding to the gradient amplifier.

Moreover, the control signals are transferred between the first power exchanging coil 318 and the second power exchanging coils 324. These control signals include a first control signal in the form of a gate control signal which aids in determining switching of the controllable switch 308, and a second control signal in the form of a feedback signal which is determined based on an output quantity of the first circuit 330.

The MRI system 300 further includes a first transmit receive element 336, a first control component 340, a second transmit receive element 338, and a second control component 342. In one example, the transmit receive elements 336, 338 may be configured to transmit and/or receive as well as modulate and/or demodulate signals. In one non-limiting example, the first and second transmit receive elements 336, 338 may include an antenna. The first control component 340 may be configured to determine a switching pattern for the active rectifier 328 and the second control component 342 may be configured to determine a switching pattern for the first circuit 330. Moreover, the first control component 340 and the second control component 342 include an H-bridge control circuit, in one non-limiting example.

In the example of FIG. 3, the first transmit receive element 336 is operatively coupled to the first power exchanging coil 318 and the first control component 340. The first control component 340 is then operatively coupled to the active rectifier 328. In one example, the first transmit receive element 336 is operatively coupled to the second transmit receive element 338 via a communications channel 346 such as Wi-Fi channel. Moreover, the second power exchanging coil 324 is operatively coupled to the second transmit receive element 338 which is in turn coupled to the second control component 342. Further, the second control component 342 may be operatively coupled to the first circuit 330. The second transmit receive element 338 is also operatively coupled to the gate drive subunit 316 and to the output of the first circuit 330.

The MRI system 300 further includes a control subunit 334. The control subunit 334 may include a processing and analyzing unit, in one non-limiting example. The control subunit 334 may transfer a polling signal to the gradient amplifier via the first transmit receive element 336, the first control component 340, the active rectifier 328, the first power exchanging coil 318, the field focusing element 320, the second power exchanging coil 324, and the second transmit receive element 338. While transmitting the polling signal, the first transmit receive element 336 aids in modulating the polling signal before it is transmitted to the gradient amplifier. Further, the modulated polling signal is provided to the first control component 340. The first control component 340 determines a switching pattern to switch the active rectifier 328 based on the modulated polling signal. Based on the switching of the active rectifier 328 the modulated polling signal may be transferred from the active rectifier 328 to the second transmit receive element 338 via the first power exchanging coil 318, the field focusing element 320, and the second power exchanging coil 324. Moreover, the second transmit receive element 338 may be configured to receive and demodulate the modulated polling signal.

Based on the polling signal, it may be determined if the health monitoring data needs to be transferred from the gradient amplifier to the control subunit 334. In one example, if the polling signal has one value (e.g., logic high) then the health monitoring data may be transferred from the gradient amplifier to the control subunit 334. However, if the polling signal has a second value (e.g., logic low), it may be indicative of the fact that the health monitoring data need not be transferred to the control subunit 334.

The health monitoring data may be transferred from the gradient amplifier to the control subunit 334 via the second transmit receive element 338 and the first transmit receive element 336. Particularly, when the first circuit 330 is an active rectifier, the health monitoring data may be transferred from the gradient amplifier to the control subunit 334 via the gate drive subunit 316, the second transmit receive element 338, the second control component 342, the first circuit 330, the second power exchanging coil 324, the field focusing element 320, the first power exchanging element 318, and the first transmit receive element 336. It may be noted that the active rectifier is a bidirectional rectifier.

In this scenario while transferring the health monitoring data, the second transmit receive element 338 may be configured to modulate the health monitoring data. Further, the modulated health monitoring data is provided to the second control component 342. The second control component 342 may determine a pattern of switching of the first circuit 330 based on the modulated health monitoring data. Based on the switching of the first circuit 330 the modulated health monitoring data may be transferred via the second power exchanging coil 324, the field focusing element 320, the first power exchanging element 318 to the first transmit receive element 336. The first transmit receive element 336 may be configured to demodulate the modulated health monitoring data. In the embodiment, where the first circuit 330 is a diode bridge, the health monitoring data may be transferred from the gradient amplifier to the control subunit 334 via the second transmit receive element 338, the communications channel 346, and the first transmit receive element 336.

At the control subunit 334, the health monitoring data may be analyzed to identify a condition of the gradient amplifier. The condition of the gradient amplifier may include a faulty condition and a healthy condition, for example. The faulty condition of the gradient amplifier may be indicative of faulty controllable switches of the gradient amplifier. In one embodiment, the health monitoring data may be transferred to a logical element 344 in the gate drive subunit 316. The health monitoring data may be employed by the logical element 344 to determine switching of the controllable switches of the gradient amplifier, in one example. The logical element 344 may be a combination of logic gates. The logical element 344 may include a combination of analog comparators and logic circuits such as, but not limited to, an AND gate, an OR gate, and latching circuits, like D-flip flops. In another embodiment, the health monitoring data of any other component of the MRI system, such as but not limited to the gradient coils and the gradient control unit may be transmitted to the control subunit 334.

In one example, the control subunit 334 transmits the gate control signal to the gate drive subunit 316 via the first transmit receive element 336, the first control component 340, the active rectifier 328, the first power exchanging coil 318, the field focusing element 320, the second power exchanging coil 324, and the second transmit receive element 338. During transfer of the gate control signal, the first transmit receive element 336 may be configured to modulate the gate control signal. Further, the modulated gate control signal is provided to the first control component 340. The first control component 340 determines switching of the active rectifier 328 based on the modulated gate control signal. Based on the switching of the active rectifier 328 the modulated gate control signal is transferred to the second transmit receive element 338 via the first power exchanging coil 318, the field focusing element 320, and the second power exchanging coil 324. At the second transmit receive element 338, the modulated gate control signal may be received and demodulated. Further, the gate control signal may be provided to the gate drive subunit 316. In another example, the gate control signal may be provided to the gate drive subunit 316 from the control subunit 334 by employing an opto-coupler, fiber optic cable, or a combination thereof.

With continued reference to FIG. 3, the first circuit 330 generates an output quantity, such as an output voltage or output current of the first circuit 330. The value of the output voltage across the first circuit 330 is maintained at a desired value. In one example, the value of the output voltage across the first circuit 330 is maintained at 20 volts. However, if the value of the output voltage across the first circuit 330 is different than 20 volts then switching of switches of the active rectifier 328 may be regulated. Based on the regulation of the switching of switches of the active rectifier 328, the value of output voltage across the first circuit 330 is maintained at 20 volts.

When the first circuit 330 is an active rectifier, the feedback signal is transferred to the active rectifier 328 via the second transmit receive element 338, the second control component 342, the second power exchanging coil 324, the field focusing element 320, the first power exchanging coil 318, the first transmit receive element 336, and the first control component 340. In particular, the feedback signal is modulated by employing the second transmit receive element 338. Further, the modulated feedback signal is transferred to the second control component 342. Based on the modulated feedback signal the second control component 342 may determine a pattern of switching the switches of the first circuit 330.

Based on switching of the first circuit 330, the modulated feedback signal is transmitted via the second power exchanging coil 324, the field focusing element 320, the first power exchanging coil 318 to the first transmit receive element 336. At the first transmit receive element 336 the modulated feedback signal is demodulated. Further, the feedback signal is provided to the first control component 340. In addition, the first control component 340 may determine the pattern of switching of the switches of the active rectifier 328. This switching of switches of the active rectifier 328 may in turn aid in regulating the output quantity of the first circuit 330.

When the first circuit 330 is a diode rectifier, the feedback signal is modulated by employing the second transmit receive element 338. Further, the modulated feedback signal is transferred to the first transmit receive element 336 via the communications channel 346. At the first transmit receive element 336 the modulated feedback signal is demodulated and is further provided to the first control component 340. Subsequently, the first control component 340 may determine the pattern of switching of the switches of the active rectifier 328. Based on the change in pattern of switching of the switches of the active rectifier 328 the output quantity of the first circuit 330 may in turn be regulated.

Furthermore, in one embodiment, the gate drive subunit 316 may provide an output signal to the control terminal 310 of the controllable switch 308 based on the gate control signal. In one example, when the gate control signal is high, a voltage of +15 volts is provided to the control terminal 310 of the controllable switch 308 thereby activating the controllable switch 308. However, if the gate control signal is low, a voltage of −5 volts is provided to the control terminal 310 of the controllable switch 308 thereby deactivating the controllable switch 308.

In an alternate embodiment, based on the health monitoring data obtained at the logical element 344 in the gate drive subunit 316 and the gate control signal provided to the gate drive subunit 316, the gate drive subunit 316 may generate a desired output signal. This output signal is provided to the control terminal 310 of the controllable switch 308. Based on the output signal of the gate drive subunit 316 the controllable switch 308 is activated or deactivated. In one example, if the gradient amplifier is in a healthy condition, the health monitoring data may be high and if the gradient amplifier is unhealthy, the health monitoring data may be low. If both the health monitoring data and the gate control signal are high then the controllable switch 308 may be activated. Moreover, if either the health monitoring data or the gate control signal is low then the controllable switch 308 may be deactivated. Therefore, if the gradient amplifier is healthy, only then the controllable switch 308 is activated.

Figure 4:
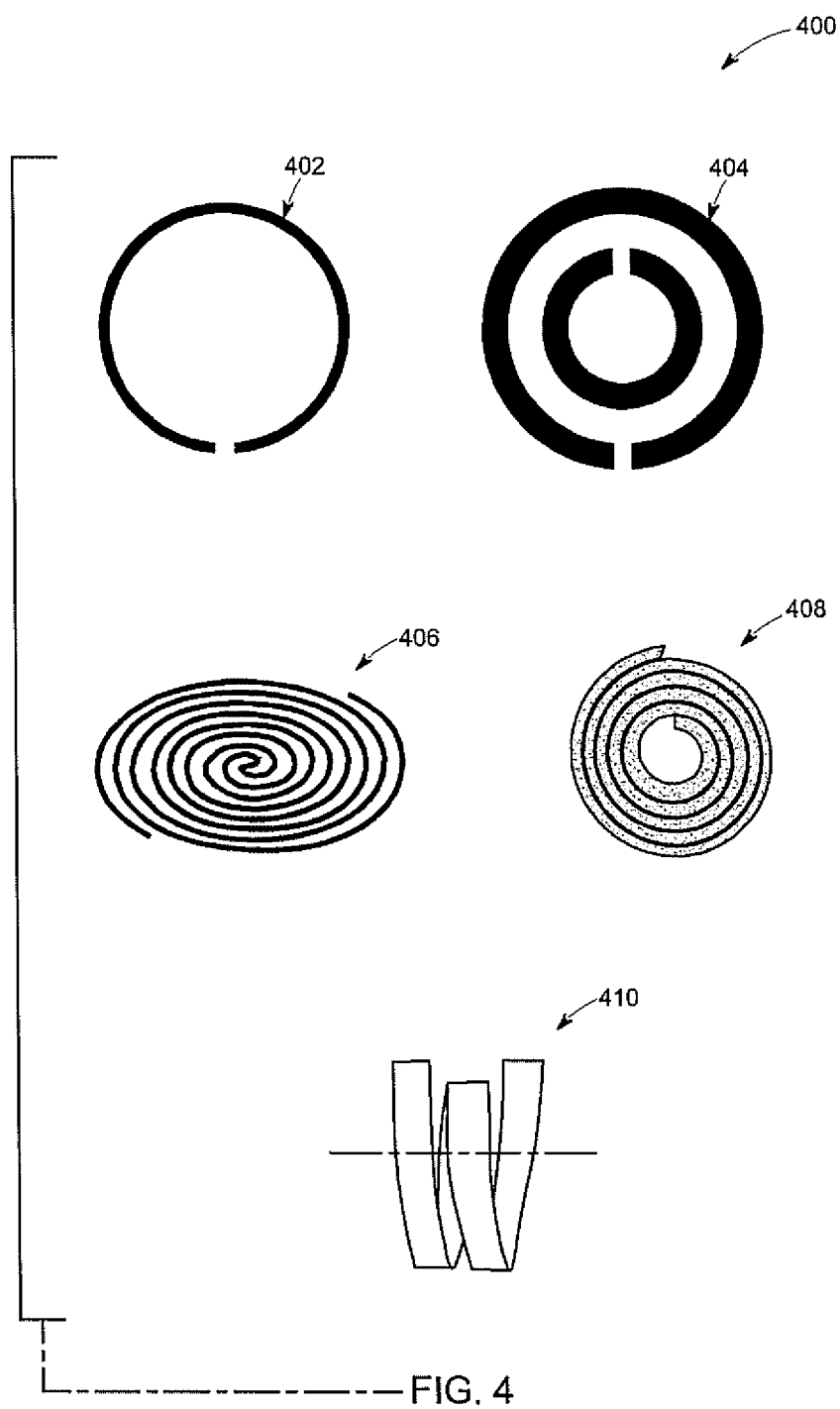
FIG. 4 is a diagrammatical representation of different resonators used as a field focusing element of the exemplary system of FIG. 1, according to embodiments of the present invention.

Turning now to FIG. 4, a diagrammatical representation 400 of different resonators used as a field focusing element in accordance with embodiments of the present invention, is presented. In one embodiment, the field focusing element, such as field focusing element 114, 226 and 320, includes a single loop coil 402. In another embodiment, the field focusing element includes multiple turns such as a split ring structure 404, a spiral structure 406, a Swiss-roll structure 408, or a helical coil structure 410. Selection of a structure of the field focusing element for a particular application is determined by size and resonant frequency of the field focusing element.

Figure 5:
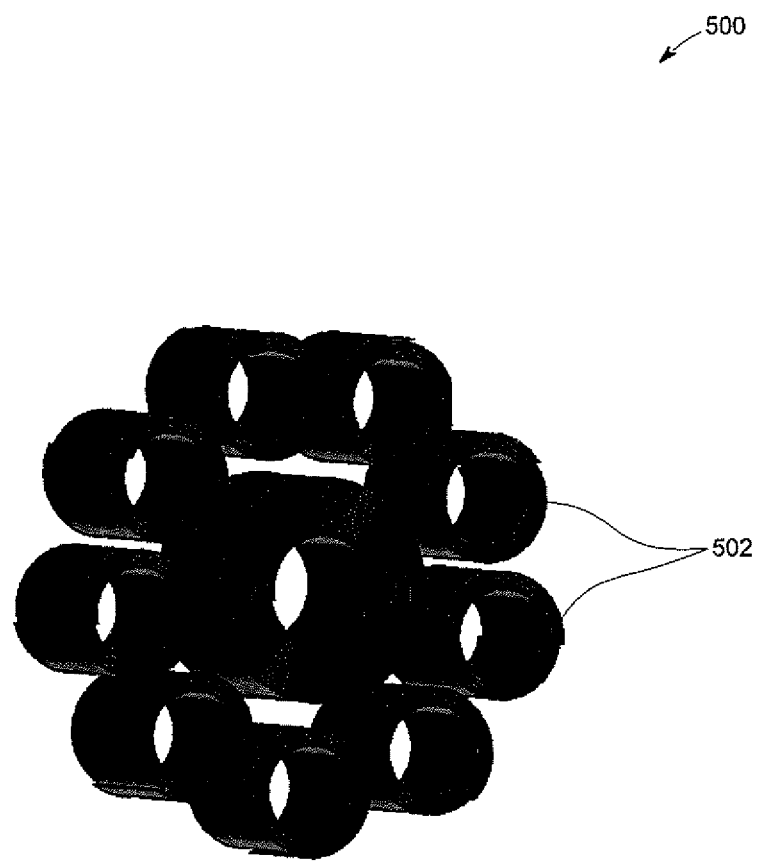
FIG. 5 is a diagrammatical representation of a plurality of resonators arranged in an array and used as the field focusing element of the exemplary system of FIG. 1, according to embodiments of the present invention.

FIG. 5 is a diagrammatical representation 500 of a plurality of resonators used as the field focusing element in accordance with embodiments of the present invention. In particular, the field focusing element 500 includes a plurality of resonators 502 arranged in an array. The plurality of resonators 502 is configured to operate as a single unit and generate a resultant magnetic field. The resultant magnetic field is generated by respective magnetic fields of each of the plurality of resonators 502 in the array interfering constructively/additively in a desired direction. However, the respective magnetic fields of each of the plurality of resonators 502 in the array interfere destructively in directions other than the desired direction. The resultant magnetic field is focused towards the second power exchanging coil.

At the second power exchanging coil the resultant magnetic field is converted into power and is further provided to the controllable switch, such as the controllable switch 308 of FIG. 3 via a gate drive subunit, such as the gate drive subunit 316. In one embodiment, each of the plurality of resonators 502 may be structurally different. Further, the plurality of resonators 502 may be configured to operate at different resonant frequencies simultaneously to enable a simultaneous bi-directional transfer of power, data, or control signals between the first power exchanging coil, such as the first power exchanging coil 108 of FIG. 1 and the second power exchanging coil 110. Although, the example of FIG. 5 depicts one arrangement of the array of resonators, other arrangement of the array of resonators is contemplated.

Figure 6:
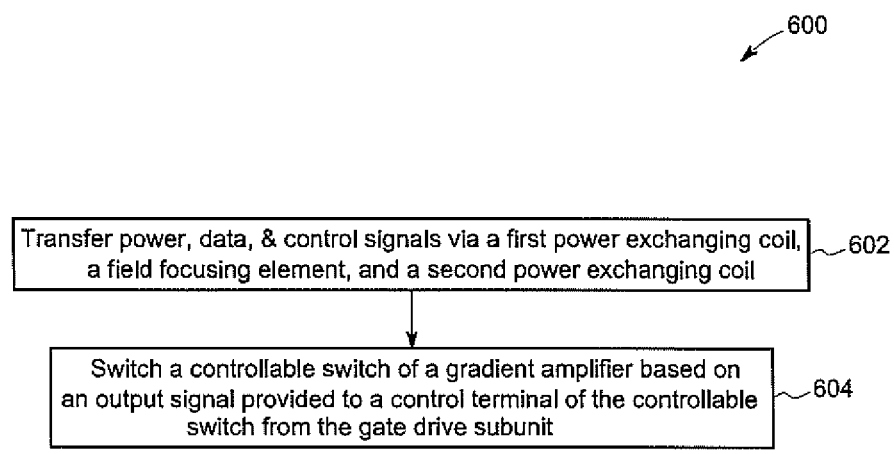
FIG. 6 is a flow chart representing an exemplary method of contactless power transfer in a magnetic resonance imaging system, according to embodiments of the present invention.

Turning now to FIG. 6, a flow chart 600 representing an exemplary method of contactless power transfer in a gate driver unit of a magnetic resonance imaging system, is presented. The method of FIG. 6 will be explained with respect to elements of FIG. 1. The method begins at block 602 where power, data, or control signals are transferred via a first power exchanging coil, a field focusing element, and a second power exchanging coil. In particular, power from a power source 106 may be transferred via a first power exchanging coil 108, a field focusing element 114, and a second power exchanging coil 110 to a gate drive subunit 104. In one non-limiting example, the power source may be a PDU. The power provided by the power source to the first power exchanging coil 108 may be transferred to the second power exchanging coil 110 via a magnetic field 112.

The control signals include a gate control signal and a feedback signal. In one embodiment, the gate control signal may be provided via a fiber optic cable, an opto-coupler, or a combination thereof. In another embodiment, the gate control signal may be provided via the first power exchanging coil 108, the field focusing element 114, the second power exchanging coil 110, or combinations thereof. Moreover, the feedback signal may be provided to the active rectifier, such as the active rectifier 328 of FIG. 3, based on the output of the first circuit, such as first circuit 330 of FIG. 3, in order to maintain the output of the first circuit 330 at a desired value.

Furthermore, the data may be transferred between the gradient amplifier and a control subunit, such as the control subunit 334 of FIG. 3, via the second power exchanging coil 110, the field focusing element 114, and the first power exchanging coil 108. The data may include a polling signal and a health monitoring data corresponding to the gradient amplifier which may be transferred based on the polling signal. In one example, the health monitoring data corresponding to the gradient amplifier maybe provided to the logical element, such as the logical element 344 of FIG. 3, in the gate drive subunit 104. The transfer of data and control signals is similar to the explanation of the transfer of data and control signals as described with respect to FIG. 3.

At block 604, a controllable switch, such as controllable switch 308 of FIG. 3, of a gradient amplifier is activated or deactivated based on an output signal provided to a control terminal, such as the control terminal 310 of FIG. 3, of the controllable switch from the gate drive subunit 104. The control terminal may include a gate terminal, in one example. In one example, the output signal may be determined by the gate control signal provided to the gate drive subunit 104 from the control subunit.

In another example, the output signal may be determined based on a combination of the gate control signal and the health monitoring data obtained at the logical element in the gate drive subunit 316. In one example, when the output signal is +15 volts the controllable switch is activated and when the output signal is −5 volts the controllable switch is deactivated.

Furthermore, the foregoing examples, demonstrations, and process steps such as those that may be performed by the system may be implemented by suitable code on a processor-based system, such as a general-purpose or special-purpose computer. It should also be noted that different implementations of the present disclosure may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository or memory.

The various embodiments of a gate driver unit as used in a MRI system and a method of contactless power transfer in the gate driver unit of the MRI system described hereinabove aids in providing efficient transfer of power to the controllable switches. Moreover, the method of contactless power transfer in the gate driver unit of the MRI system aids in placing many of the subsystems of the MRI system in a scan room thereby reducing the footprint of an equipment room. In particular, the gradient amplifier of the MRI system may be placed in the scan room. Furthermore, according to aspects of the present disclosure, the gate driver unit as used in the MRI system provides high dv/dt immunity and desired isolation.

In addition, the novel gate driver unit described herein and as used in a MRI system is devoid of ferrites, in turn minimizing saturation issues in the scan room. Moreover, the gate driver unit as used in a MRI system allows transmission of power, control signals, and data at resonant frequencies which does not interfere with Larmor or precessional frequency of the MRI system. Accordingly, imaging quality of the MRI system is not affected. Furthermore, the various embodiments of the gate driver unit and the method of contactless power transfer may find applications in high voltage power converters, circuit breakers and other residential and commercial power distribution applications. Also, the method of contactless power transfer may be employed in other medical systems.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

What is claimed is:

1. A gate driver unit comprising:
   a first power exchanging coil operatively coupled to a power source;
   a second power exchanging coil configured to receive power from the first power exchanging coil via a magnetic field;
   a field focusing element disposed between the first power exchanging coil and the second power exchanging coil and configured to focus the magnetic field onto the second power exchanging coil;
a compensation coil disposed between the field focusing element and the second power exchange coil and configured to compensate a change in phase angle resulting from a misalignment of the first power exchanging coil and the second power exchanging coil;
a first circuit coupled to the second power exchanging coil; and
a gate drive subunit operatively coupled to the first circuit and configured to provide an output signal to a control terminal corresponding to a controllable switch of a second circuit.

2. The gate driver unit of claim 1, wherein the compensation coil is further configured to match an impedance of the first power exchanging coil and an impedance of the second power exchanging coil.

3. The gate driver unit of claim 1, wherein the field focusing element operates at at least one resonant frequency.

4. The gate driver unit of claim 3, wherein the compensation coil operates at a resonant frequency different from the at least one resonant frequency of the field focusing element.

5. The gate driver unit of claim 1, wherein the first power exchanging coil and the second power exchanging coil are configured to handle a bidirectional flow of at least one of the power, data, and control signals between the first power exchanging coil and the second power exchanging coil.

6. The gate driver unit of claim 4, wherein one or more of the power, the data, and the control signals are transferred simultaneously at the at least one resonant frequency.

7. The gate driver unit of claim 4, wherein one or more of the power, the data, and the control signals are transferred alternately at the at least one resonant frequency.

8. The gate driver unit of claim 1, wherein the control terminal of the controllable switch comprises a gate terminal.

9. The gate driver unit of claim 1, wherein the first power exchanging coil comprises a transmitter coil and the second power exchanging coil comprises a receiver coil.

10. The gate driver unit of claim 1, wherein the first power exchanging coil comprises a receiver coil and the second power exchanging coil comprises a transmitter coil.

11. The gate driver unit of claim 1, wherein the field focusing element is configured to enhance coupling between the first power exchanging coil and the second power exchanging coil.

12. The gate driver unit of claim 1, wherein the field focusing element comprises at least one resonator.

13. The gate driver unit of claim 1, wherein the field focusing element comprises a plurality of resonators arranged in an array and the plurality of resonators configured to operate as a single unit such that a resultant magnetic field produced from the plurality of resonators is focused onto the second power exchanging coil.

14. The gate driver unit of claim 1, wherein the first circuit comprises at least one of an active rectifier and a diode rectifier.

15. A magnetic resonance imaging system comprising:
a gradient amplifier disposed proximate to a magnet assembly of the magnetic resonance imaging system and comprising a plurality of controllable switches;
a gate driver unit operatively coupled to the gradient amplifier and comprising
a first power exchanging coil operatively coupled to a power source;
a second power exchanging coil configured to receive power from the first power exchanging coil via a magnetic field;
a field focusing element disposed between the first power exchanging coil and the second power exchanging coil and configured to focus the magnetic field onto the second power exchanging coil;
enhance coupling between the first power exchanging coil and the second power exchanging coil;
a first circuit coupled to the second power exchanging coil; and
a gate drive subunit operatively coupled to the first circuit and configured to provide an output signal to a control terminal corresponding to the plurality of controllable switches.

16. The system of claim 15, wherein the first power exchanging coil and the second power exchanging coil are separated by at least one of an insulator and an air gap.

17. The system of claim 15, wherein the first power exchanging coil and the second power exchanging coil are configured to handle a bidirectional flow of at least one of the power, data, and control signals between the first power exchanging coil and the second power exchanging coil at least one resonant frequency.

18. The system of claim 17, further comprising a control subunit operatively coupled to the gate drive subunit and configured to
transfer a first data to the gradient amplifier;
receive a second data from the gradient amplifier based on the first data; and
transmit a first control signal to the gate drive subunit.

19. The system of claim 18, wherein the second data comprises a health monitoring data corresponding to the gradient amplifier.

20. The system of claim 15, wherein the power source comprises a constant voltage source coupled to an active rectifier.

21. The system of claim 20, wherein a second control signal is transferred to the active rectifier via at least one of the second power exchanging coil, the field focusing element, and the first power exchanging coil based on an output voltage of the first circuit.

22. The system of claim 15, wherein the gate driver unit is disposed proximate to the magnet assembly of the magnetic resonance imaging system.

23. The system of claim 22, wherein the gradient amplifier and the gate driver unit are disposed in a scan room.

24. A method of contactless power transfer in a magnetic resonance imaging system comprising:
transferring power from a power source via a first power exchanging coil, a field focusing element, and a second power exchanging coil to a gate drive subunit;
switching a controllable switch of a gradient amplifier based on an output signal provided to a control terminal of the controllable switch from the gate drive subunit; and
transferring data between the gradient amplifier to a control subunit via the gate drive subunit, the second power exchanging coil, the field focusing element, and the first power exchanging coil.

25. The method of claim 24, further comprising transferring a control signal from the control subunit to the gate drive subunit via the first power exchanging coil, the field focusing element, and the second power exchanging coil.

26. The method of claim 25, wherein transferring the power, the control signal, and the data comprises transferring the power, the control signal, the data, or combinations thereof at at least one resonant frequency.

27. The method of claim 25, further comprising determining the output signal based on at least one of the control signal and the data.

28. The method of claim 24, further comprising compensating a change in phase and matching impedance between the first power exchanging coil and the second power exchanging coil using a compensation coil.

* * * * *